United States Patent [19]

Evans

[11] Patent Number: 4,715,718
[45] Date of Patent: Dec. 29, 1987

[54] METHOD AND APPARATUS FOR ON-LINE MONITORING OF LAMINATE BOND STRENGTH

[75] Inventor: John C. Evans, Midland, Mich.

[73] Assignee: The Dow Chemical Company, Midland, Mich.

[21] Appl. No.: 748,363

[22] Filed: Jun. 24, 1985

[51] Int. Cl.⁴ ............................................. G01N 21/47
[52] U.S. Cl. ..................................... 356/446; 356/429
[58] Field of Search ............... 356/445, 446, 447, 448, 356/369, 237, 429, 430, 431; 250/571, 572

[56] References Cited

U.S. PATENT DOCUMENTS

| | | | |
|---|---|---|---|
| 2,947,212 | 8/1960 | Woods | 356/369 |
| 3,693,025 | 9/1972 | Brunton | 356/446 |
| 3,832,065 | 8/1974 | Sullivan et al. | 356/447 |
| 4,015,127 | 3/1977 | Sharkins | 356/369 |
| 4,172,666 | 10/1979 | Clark | 356/431 |
| 4,583,861 | 4/1986 | Yamaji et al. | 356/446 |

Primary Examiner—R. A. Rosenberger
Attorney, Agent, or Firm—Andrew E. Pierce; Timothy S. Stevens

[57] ABSTRACT

A method and apparatus for the on-line determination of the bonding strength of a plural layer laminate having at least one outer layer transparent to electromagnetic radiation, said method comprising: directing a collimated beam of electromagnetic radiation onto the substantially flat surface of said laminate at an incident angle substantially greater than a normal to the surface of said laminate; measuring the reflected intensity of said electromagnetic radiation at two substantially different diffuse reflectance angles; converting said reflected intensity to an intensity ratio by dividing the greater intensity value by the lesser intensity value to obtain a value which is proportional to the adhesion of the laminate based upon a pre-determined relationship of the bonding strength of said laminate and the value of said intensity ratio.

15 Claims, 3 Drawing Figures

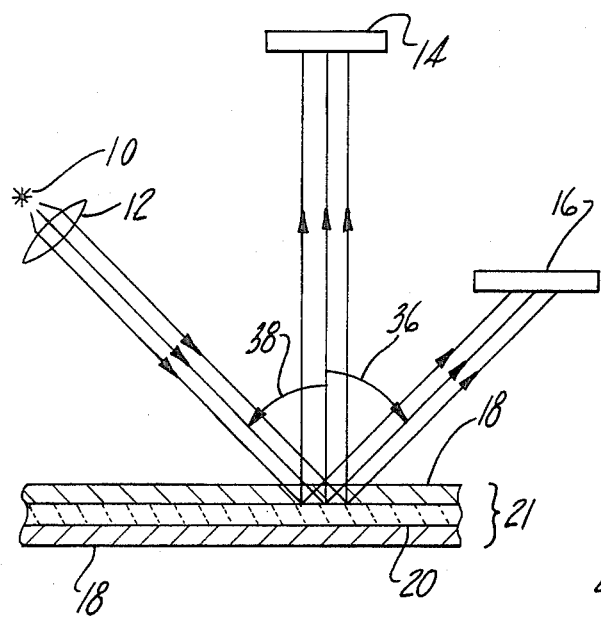
Fig-1
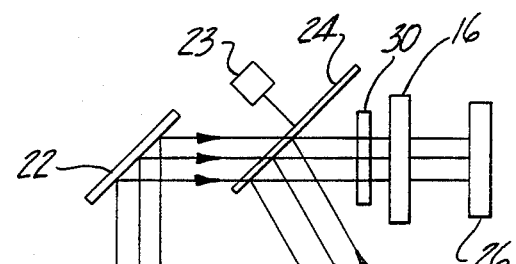
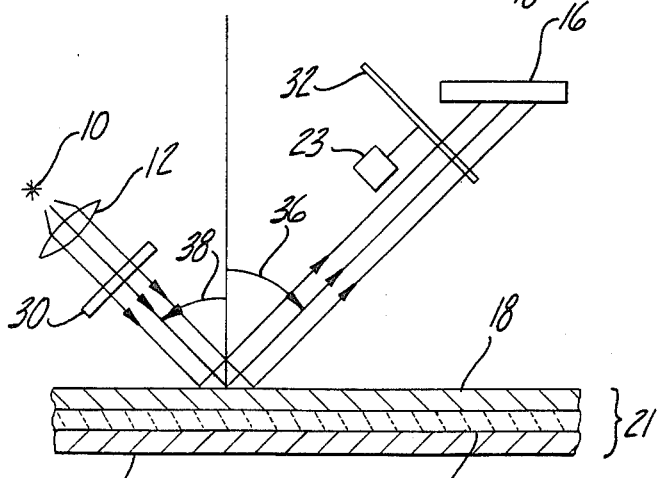
Fig-2
Fig-3

METHOD AND APPARATUS FOR ON-LINE MONITORING OF LAMINATE BOND STRENGTH

BACKGROUND OF THE INVENTION (1) Field of the Invention

The invention relates to a method and apparatus for the on-line determination of laminate bond strength by a nondestructive, noncontact method.

(2) Description of the Prior Art

Measuring the bonding strength of a plural layered laminate whether prepared utilizing an adhesive material or whether prepared by heat sealing a thermoplastic layer of the laminate to a second laminate layer has up until now been accomplished by a tedious, time consuming destructive method involving peeling the laminate apart and measuring the force required to delaminate the assembly. Such assemblies as plastic, wood, and fabric laminates are often utilized. The quality of such laminates can vary depending upon the strength of the adhesive bond. It would be desirable to obtain an indication of the strength of the adhesive bond during the preparation of the laminate on high speed lamination equipment. Great savings could be made if the bond strength could be determined on-line prior to the preparation of large amounts of defective laminate.

The on-line monitoring of the specific surface of mechanical pulps by measuring the light scattering characteristics of the pulp sample is disclosed in U.S. Pat. No. 4,441,960. The on-line measurement of inclusions in pulp slurries is disclosed in U.S. Pat. No. 4,402,604. In this method an apparatus for measuring inclusions comprises a series of photosensitive devices arranged to receive light reflected from or transmitted through the pulp material.

In U.S. Pat. No. 3,574,470 there is disclosed a method and device for detecting abnormal voids in a low density material such as polyurethane foam by measuring the light reflected from the foam; the intensity of the reflected light decreasing when the incident light is beamed into a low density material having an abnormal void. In U.S. Pat. No. 4,215,939, a method and apparatus is disclosed for measuring the presence of a glue drop on the reflective inner surface of a closure by directing collimated light onto the closure and measuring the amount of light remaining collimated after reflection from the closure.

Other methods of measuring the bond strength of an adhesive material utilized to bond layers of a laminate are disclosed in U.S. Pat. No. 3,770,547 and U.S. 3,740,290 wherein a method is disclosed to provide for development of a color in the adhesive to indicate sufficient reactivity of the adhesive. In U.S. Pat. No. 4,232,559 a means is disclosed for determining the area of contact of an adhesive material with a substrate by comparing the amount of light reflected through the right angle sides of a prism when the hypotenuse face of the prism is in contact with the adhesive as compared to when the hypotenuse face is not in contact with the adhesive; the adhesive having an index of refraction higher than that of the prism.

SUMMARY OF THE INVENTION

The invention relates to methods and apparatus for determining the adhesive bond strength of a laminate having plural substrate layers which are transparent to electromagnetic radiation on at least one outer layer of said laminate. By the method of the invention, collimated electromagnetic radiation is directed onto one surface of the laminate at an incident angle substantially greater than a normal to the surface of said laminate. The intensity of the reflected electromagnetic radiation, in one embodiment of the invention, having a wave length in the visible, ultraviolet, or infrared portions of the spectrum, is measured at two substantially different angles of diffuse reflection. Both incident and reflected light can be polarized or non-polarized in this method of measurement. The measured intensity of reflected light is converted to a diffuse intensity ratio so as to cancel out variations in intensity of the light source. In another embodiment of the invention, reflected light from a polarized light source is measured at only one angle of reflectance; the reflected light being first passed before measurement through a polarizer oriented parallel to the plane of polarized incident light or alternately through a polarizer oriented perpendicular to the plane of the polarized incident light. The apparatus can include a modulator through which the collimated incident light is passed prior to being projected onto the surface of the laminate and a detector for measuring the diffuse reflection, the output signal of which is amplified by an amplifier tuned to the modulator frequency.

BRIEF DESCRIPTION OF THE DRAWINGS

FIG. 1 shows schematically an apparatus for detecting light which is reflected from the surface of a laminate upon which collimated light has been projected.

FIG. 2 shows schematically an apparatus utilized for detecting light reflected at two angles from a laminate upon which collimated light has been projected. A single detector is utilized in conjunction with modulator for modulating the polarized collimated incident light and a tuned amplifier which is tuned to the modulator frequency for amplification of the polarized reflected light detector output signal.

FIG. 3 shows schematically an apparatus for detecting light reflected from the surface of a laminate which has been exposed to collimated light which has been modulated and polarized. The reflected light is passed through parallel or crossed polarizers prior to detection.

DETAILED DESCRIPTION OF THE DRAWINGS

Referring to FIG. 1 electromagnetic radiation in the form of visible, ultraviolet, or infrared radiation is emitted from source 10 located at the focal point of a converging lens 12. This causes the radiation emanating from the lens 12 to be collimated. The collimated radiation is projected onto the surface of laminate 21 which is transparent in at least one layer thereof. Laminant 21 is composed of layers 18 and 20. The light is reflected and scattered from the laminate layers 18 and 20 and detected by detectors 14 and 16. Detector 16 is positioned so as to be receptive to receiving diffuse reflection from laminate 21 wherein the diffuse reflection is at or near the optimum value of the diffuse reflection and scattered radiation emanating from laminate 21. Detector 14 is positioned to receive diffuse reflection and scattered radiation from surface 18 at an angle 38 normal or close to normal to said surface. The reflected intensity values obtained are converted to a diffuse intensity ratio by dividing the diffuse intensity at the optimum intensity angle 36 for the sample laminate 21 by the intensity at an angle at or close to normal to the surface of laminate 21. This value is proportional to the bonding strength of said laminate based upon a predetermined relationship of the bonding strength of said laminate and the value of said diffuse intensity ratio.

In alternative embodiments of the invention, as shown in FIGS. 2 and 3, a modulator 28 and a polarizer 30 are interposed between the surface of the laminate 21 and the collimated rays of radiation emanating from lens 12. A second polarizer 30 is shown in FIG. 2 as interposed between mirror 24 and detector 16. The use of a modulator is designed to provide a practical means of canceling out the effect of extraneous light on the detector 16. Also shown in FIGS. 2 and 3 is the use of a single detector for the diffuse reflection and scattered radiation emanating from laminate 21. In the embodiment shown in FIG. 2, mirrors 22 and 24 direct the diffuse reflection and scattered radiation emanating from laminate 21 toward a single detector 16, the output signal of which is amplified by amplifier 26 which is tuned to the frequency of modulator 28. Mirror 24 is a rotating disk with a mirror on one half the surface of said disk, the remaining half of the surface being clear. This arrangement permits diffuse reflection and scattered radiation emanating from laminate 21 at a normal or close to normal reflection angle 38 to be sequentially detected by detector 16 for comparison with the diffuse reflected and scattered radiation emanating from laminate 21 at the optimum intensity angle 36. Mirror 24 is rotated by a motor 23 or other suitable means. In the embodiment shown in FIG. 3, the collimated radiation is, in addition to being modulated with modulator 28, passed through polarizer 30 prior to being projected onto the surface 18 of laminate 21. The reflected radiation is detected at a single angle of diffuse reflection, preferably the angle of optimum value, from surface 18 of laminate 21 utilizing rotating disk 32 made up of two orthogonal polarizers so as to provide sequentially both parallel polarized radiation and radiation passed through crossed polarizers to detector 16. The greater value intensity of the reflected parallel polarized radiation divided by the lesser value intensity of the reflected radiation passed through the crossed polarizers (incident radiation polarizer perpendicular to reflected light polarizer) provides a diffuse intensity ratio which is utilized to cancel out any variation in the intensity of the radiation received from source 10. This ratio also provides a measure of the bonding strength of the laminate based upon a predetermined relationship of the bonding strength of said laminate and the value of said diffuse intensity ratio.

In the preferred embodiments of the invention, the source of electromagnetic radiation 10 is a source of visible light which may or may not be monochromatic. The wave length used should not be absorbed to a substantial extent by the laminate materials or very little will reach the radiation detector and sensitivity will be poor. A laser beam is a convenient form of incident electromagnetic radiation. The angle of incidence 38 of the electromagnetic radiation directed upon surface 18 of laminate 21 is generally about 10° to about 80°, preferably about 20° to about 70°, and most preferably is about 40° to about 50° although the angle of incidence is not critical. The angle of incidence 38 is measured with respect to a normal to the surface of said laminate. The optimum diffuse reflectance angle 36 is that angle at which the diffusely reflected and scattered radiation reaches its maximum value for the particular laminate. It is measured with respect to a normal to the surface of said laminate and is a function of the smoothness of the laminate 21. While two detectors are shown schematically in FIG. 1 for use in measuring the intensity of radiation scattered from surface 18 of laminate 21, a more practical apparatus is shown schematically in FIGS. 2 and 3 in which a single detector is utilized. As indicated above, it is desirable in one embodiment of the invention to measure the radiation scattered from the laminate at two scattering angles. A scattering angle of close to 0° and the angle which the radiation is scattered at an optimum value can be arbitrarily chosen. The measurement at or close to 0° provides a reference value against which the intensity at the optimum scattering angle can be continuously compared. In this way variations in the electromagnetic radiation source, both short and long term, are automatically canceled out by dividing the greater value of the reflected radiation at the optimum scattering angle by the lesser value at 0° (normal to the surface).

The use of a single detector for the intensity of scattered radiation is a preferred embodiment of the invention since it is known that such radiation detectors whether photoconductive, photogalvanic, photoelectric, etc. change in their sensitivity with time. Therefore the use of a single detector for measuring the light scattered at two angles of reflection measured by a single detector provides greater reliability in the apparatus of the invention.

The use of a modulator as a part of the apparatus of the invention is a preferred embodiment of the invention since it is likely that in the commercial use of the apparatus of the invention the measurements will be made in a well lighted factory and the use of a modulator to modulate the collimated light emanating from light source 10 assures that the diffuse reflectance readings will not be affected by the level of extraneous light present in the environment. Where a modulator of the collimated light is utilized prior to directing the incident light onto surface 18 of laminate 21, it is desirable to utilize subsequent to the detection of the diffuse reflection emanating from surface 18 of the laminate 21, an amplifier which is tuned to the modulator frequency. In this way only the modulated portion of the diffuse reflectance detector output signal is amplified and thus the effect of the extraneous light falling upon surface layer 18 of laminate 21 is canceled out. The circuitry necessary to provide the modulated collimated light and the amplifier tuned to the modulator frequency for amplifing the modulated detector output signal are well known to the art and no further description thereof need be made here. Where a single detector is utilized to measure the intensity of the diffuse reflection emanating from surface 18 of laminate 21, the two signals received by the detector can be separated electronically and the ratio of the intensity values of the signals can be displayed directly to the operator of the laminating machine, or recorded for future study or fed into a computer control system which regulates the laminate production line.

The calibration of the diffuse reflection ratio obtained must be made utilizing standard laminates with known bond strength properties evaluated in the laboratory by means of the usual tedious, destructive test methods presently established. For example, in a paper web to plastic film laminate, the bonding strength can be evaluated by peeling the laminate apart and measuring the force necessary to separate the laminate. Alternatively, the rate of water absorption of the laminate can be utilized as a measure of bonding strength in view of the fact that the laminate will absorb water more rapidly when it is poorly bonded as compared to when it is firmly bonded. This is because less of the paper web is available to absorb water where more of the web is embedded in the plastic film as the result of the bonding process.

For on-line monitoring of the bonding strength of a laminate, continuous evaluation of the laminate is necessary as it moves through the lamination machine and toward the windup end of the machine. Generally the apparatus of the invention for evaluating the bonding strength of a laminate will be mounted within a suitable protective container which will protect the components from severe surroundings such as contaminated air, vibration, and heat. Should it be necessary to monitor the bonding strength across the web as the laminate moves through the laminating machine from the bonding section toward the windup section of the machine, the apparatus can be suspended across the width of the laminate on a rail with a suitable drive mechanism to move it across the web in a regular manner so as to sample the bonding strength of the laminate along a zigzag path. The methods for mounting a monitoring device of this type are well known in the prior art and no further description will be made thereof. If it is found that the bonding strength of the laminate is invariably uniform from one side of the laminate web to the other and the variation in bonding strength only occurs across the web of the laminate from time to time, then a single fixed unit for assessing the bonding strength of the laminate will provide a less costly means of monitoring the bonding strength of the laminate. The output can be usefully employed to control the production process automatically if the process control computer is programed for closed-loop control of the process. In this case the bonding strength apparatus of the invention upon detecting a drift of the laminate away from satisfactory bonding strength would signal to the control computer which would in turn signal the desired process change required to bring the bonding strength of the laminate back into an acceptable range.

Whether the method of the invention involves making measurements at two scattering angles of diffuse reflection or whether the collimated light source is also polarized so that the incident light striking the surface of the laminate is polarized, thus permitting the measurement of the intensity of the diffuse reflection and scattered radiation emanating from the laminate at a single polarized diffuse reflection angle, the use of a modulator a single detector and a tuned amplifier for the detector signal will permit the calculation of an intensity ratio which will cancel out variations in the incident light intensity. The reflected light can be measured after passing through both parallel or crossed polarizers, said polarizers being oriented relative to the polarizer placed in the path of the incident beam of light. These modifications of the method of the invention can be utilized so as to provide an evaluation of the bonding strength of the laminate which can be electronically displayed, automatically recorded, or fed into a computer to provide closed-loop control of the lamination process. The use of the apparatus of the invention can result in considerable savings by allowing detection of laminate bonding strength which is outside an acceptable range (whether excessively bonded or insufficiently bonded) and therefore a reduction in off grade laminate can be obtained.

The apparatus of the invention is applicable to measuring the bonding strength of a laminate where at least one layer of the laminate will transmit and scatter incident electromagnetic radiation. If necessary, the electromagnetic radiation can be provided from a laser source. The apparatus of the invention is suitable for the evaluation of the bonding strength of many diverse forms of laminate having at least one layer transparent to electromagnetic radiation. By establishing the relationship of the laminate bonding strength and/or the rate of water absorption of the laminate to the diffuse reflectance obtained subsequent to directing incident radiation onto the surface of the laminate, a measure of bonding strength can be obtained. It is believed that the measurement of the diffuse reflectance emanating from a laminate is an extremely sensitive means of assessing the laminate bonding strength. It has also been found that with excessively bonded plastic film-paper laminates which have been laminated by heat sealing, the layers of laminated material tend to fuse and become one layer with a reduction in the rate of water absorption. With inadequately bonded layers of a laminate, there is only an intermittent fusion of the layers of the laminate and the rate of water absorption increases. Thus the degree of fusion of the layers can be evaluated directly by measuring the diffuse reflection emanating from the layers of the laminate.

The following examples illustrate the various aspects of the invention but are not intended to limit its scope. Where not otherwise specified throughout this specification and claims, temperatures are given in degrees centigrade, and parts, percentages, and proportions are by weight.

In the following examples, a three layer flexible water absorbent laminate was evaluated for bonding strength by evaluating the diffuse reflectance ratio obtained in several different ways as shown in Examples I to IV. The laminate evaluated was a plastic film with a paper web laminated to each surface of the film. The incident beam of light was directed onto the paper web surfaces of the laminate and diffuse intensity values determined for each side of the laminate. The plastic film and paper web flexible absorbent laminates evaluated were made in accordance with the procedure described in U.S. Pat. No. 4,117,184 and U.S. Pat. No. 4,293,609, both incorporated herein by reference. The laminates were not passed through a crushing or cracking zone wherein the film is broken into a plurality of pieces which remain substantially bonded to the paper substrate. The apparatus and method of the invention is particularly suitable for on-line evaluation of the bonding strength of such laminates prior to their being crushed during a later stage of processing.

EXAMPLE I

Utilizing a commercially prepared absorbent laminate similar to that described in U.S. Pat. No. 4,117,184 a large number of measurements were made on different samples measuring 4 centimeters by 4 centimeters of said three layer laminate. The samples were cut in about equal numbers from three regions across the width of the laminate; said three regions located near the left, the center, and the right sides of said laminate and taken from three different commercially prepared rolls of laminate. It was found that the variation across the total width of the laminate web was no larger than the variations within each of the three regions and for this reason the data were combined to calculate averages for the entire web width at each location.

To obtain the reflected light intensity readings, a Brice-Phoenix light scattering photometer modified for use as a photogoniometer was used. Each of the 4 centimeter by 4 centimeter samples of laminate was attached to a vertical metal support located at the center of a sample support table and an area of about 1 centimeter by 1 centimeter was illuminated uniformly by an almost parallel beam of green (546 nanometer) vertically polarized light. In the following examples, the incident light directed at the surface of the laminate was at an angle of 45°. It was found that for reproducible diffuse reflectance readings that the flatness of the illuminated region of the sample must be assured. This was achieved by using double-coated tape to adhere the sample to the blackened metal support. Intensity measurements were taken at the optimum angle of diffuse reflectance for the sample which was found to be 70°. The reflectance was measured using polarized incident light and with the polarizer in the path of the reflected beam alternatively oriented parallel or perpendicular to the incident beam polarizer. The ratio of the diffuse reflectance (measured utilizing a polarizer for the reflected beam which is oriented parallel to the incident beam polarizer) to the reflectance (measured utilizing the reflected beam polarizer oriented perpendicular to the incident beam polarizer) was calculated. The laminating process utilized to prepare the samples of commercial absorbant laminate provides for the bonding of the paper and plastic film layers of the laminate at two different locations in the production line. Thus the plastic film is bonded to one of the paper layers and successively bonded on the opposite surface of the plastic film to a second paper layer. Because of this, differences in bonding quality between the two sides of the laminate may result and therefore both sides of the laminate were examined by the method of the invention. In addition, the paper utilized in the preparation of the laminate is characterized as having a fine corrugated structure which, in these laminates, was oriented so that the furrows ran approximately at right angles to the machine direction of the laminate. The data for Example I were collected for the condition where the machine direction was oriented perpendicular to the direction of the polarizer in the path of the incident beam of light. That is the machine direction was horizontal to the direction of the polarizer.

Table No. 1 provides a summary of the results obtained. Each value given for the reflectance ratio was obtained by taking the mean of the data obtained for between 9 and 20 samples taken from the same region of the roll of the commercially prepared laminate. In the third column of Table No. 1 there is provided the results of a destructive, tape adhesion test which is commonly used to asses the bonding quality of the laminate. These tape adhesion test results are provided to show the correlation between the adhesion of the laminate as evaluated by this test and the adhesion of the laminate as evaluated by the method of the invention.

TABLE No. 1

Laminate Bond Strength Evaluation by Diffuse and Scattered Reflection Intensity Measurement

| Sample[1] | Intensity Ratio[2] Laminate | | Tape Adhesion Test[3] |
|---|---|---|---|
| | Inside Surface | Outside Surface | |
| A | 1.55 | 1.47 | 31 |
| B | 1.67 | 1.49 | 33 |
| C | 1.70 | 1.56 | 40 |

[1]Machine direction of samples oriented perpendicular to the direction of the polarizer mounted in the path of the incident beam of light.
[2]Intensity Ratio is calculated by dividing the diffuse and scattered radiation intensity, reflected from the laminate at an angle of 70° to normal, using parallel oriented polarizers by the diffuse and scattered radiation intensity, reflected at an angle of 70° to normal, using perpendicularly oriented polarizers.
[3]arbitrary units of adhesion used.

EXAMPLE II

The same laminate samples were used as in Example I and the same means of measurement were utilized. Only one change in procedure occureed, namely the samples were evaluated with the machine direction parallel with the direction of the polarizer in the path of the incident beam of light, that is in the vertical direction. The results obtained are shown in Table No. 2 where each value given for the intensity ratio was obtained by taking the mean of data obtained from measurement of between 9 and 20 samples of laminate. Also provided in column three of Table No. 2, for comparison purposes only, are the results of a destructive, quality control test of the rate of water uptake by the laminate.

TABLE No. 2

Laminate Bond Strength Evaluation by Diffuse and Scattered Reflection Intensity Measurement

| Sample[1] | Intensity Ratio[2] Laminate | | Water Uptake Test[3] |
|---|---|---|---|
| | Inside Surface | Outside Surface | |
| A | 1.51 | 1.41 | 21 |
| B | 1.57 | 1.44 | 24 |
| C | 1.58 | 1.48 | 37 |

[1]Machine direction of samples oriented parallel to the direction of the polarizer mounted in the path of the incident beam of light.
[2]Intensity Ratio is calculated by dividing the diffuse and scattered radiation intensity, reflected from the laminate at an angle of 70° to normal, using parallel oriented polarizers by the diffuse and scattered radiation intensity, reflected at an angle of 70° to normal, using perpendicularly oriented polarizers.
[3]arbitrary units of water uptake used.

EXAMPLE III

The same samples of laminate were used and evaluated utilizing the apparatus described in Example I to determine an intensity ratio except that the intensity ratio was obtained by measuring the reflected and scattered radiation first at an optimum angle of scattering of 70° to normal and then measuring the intensity of reflected and scattered ratiation at the normal to the surface of the laminate. The angle of incidence was 45° in all tests. In this series of evaluations, all the samples of laminate were mounted with the machine direction of the laminate oriented vertically and parallel to the direction of the incident beam of vertically oriented polarized light. The polarizer mounted in the path of the reflected beam was first oriented vertically, parallel to the polarizer mounted in the incident beam, and subsequently oriented horizontally, that is, perpendicular to the polarizer mounted in the path of the incident beam of light. In Table No. 3 the intensity ratios are tabulated for the various samples evaluated.

TABLE No. 3

Laminate Bond Strength Evaluation by Diffuse and Scattered Reflection Intensity Measurement

| | Intensity Ratio of Laminate[2] | | | |
|---|---|---|---|---|
| | Inside Surface | | Outside Surface | |
| Sample[1] | (parallel polarizers) | (perpendicular polarizers) | (parallel polarizers) | (perpendicular polarizers) |
| A | 2.07 | 1.55 | 1.94 | 1.53 |
| B | 2.17 | 1.59 | 2.00 | 1.57 |
| C | 2.25 | 1.65 | 2.15 | 1.66 |

[1]Machine direction of samples oriented perpendicular to the direction of the polarizer mounted in the path of the incident beam of light.
[2]Intensity Ratio is calculated by dividing the diffuse and scattered radiation intensity, reflected from the laminate at an angle of 70° to normal, using parallel oriented polarizers by the diffuse and scattered radiation intensity, reflected at an angle of 70° to normal, using perpendicularly oriented polarizers.

EXAMPLE IV

The same laminate samples were utilized as in Example III and the same measurements were made but in this evaluation all of the samples were mounted so that the machine direction was horizontal and perpendicular to the direction of the polarizer mounted in the path of the incident beam of light. The results of the measurements obtained are provided in Table No. 4.

TABLE No. 4

Laminate Bond Strength Evaluation by Diffuse and Scattered Reflection Intensity Measurement

| | Intensity Ratio of Laminate[2] | | | |
|---|---|---|---|---|
| | Inside Surface | | Outside Surface | |
| Sample[1] | (parallel polarizers) | (perpendicular polarizers) | (parallel polarizers) | (perpendicular polarizers) |
| A | 1.69 | 1.34 | 1.74 | 1.40 |
| B | 1.92 | 1.43 | 1.79 | 1.42 |
| C | 2.05 | 1.58 | 1.97 | 1.52 |

[1]Machine direction of samples oriented parallel to the direction of the polarizer mounted in the path of the incident beam of light.
[2]Intensity Ratio is calculated by dividing the diffuse and scattered radiation intensity, reflected from the laminate at an angle of 70° to normal, using parallel oriented polarizers by the diffuse and scattered radiation intensity, reflected at an angle of 70° to normal, using perpendicularly oriented polarizers.

While this invention has been described with reference to obtain specific embodiments, it will be recognized by those skilled in the art that many variations are possible without departing from the scope and spirit of the invention, and it will be understood that it is intended to cover all changes and modifications of the invention disclosed herein for the purposes of illustration which do not constitute departures from the spirit and scope of the invention.

The embodiments of the invention in which an exclusive property of priviledge is claimed are defined as follows:

1. A method for the on-line determination of the bonding strength of a plural layer laminate having at least one inner and one outer layer, said outer layer being transparent to electromagnetic radiation, said method comprising:
   (a) directing a collimated beam of electromagnetic radiation transmitted onto a surface of said inner layer through said transparent outer layer at an incident angle substantially greater than a normal to the surface of said laminate;
   (b) measuring the scattered and diffusely reflected intensity value of said electromagnetic radiation reflected from said inner layer at two substantially different diffuse reflectance angles;
   (c) converting said reflected intensity value to a diffuse intensity ratio derived value which is proportional to the adhesion of the laminate based upon a predetermined relationship of the bonding strength of said laminate and said derived value.

2. The method of claim 1 wherein said electromagnetic radiation is directed onto said laminate in a beam of electromagnetic radiation which has a wave length in the visible, near ultraviolet, or near infrared length portion of the spectrum, wherein said light is projected at an incident angle of about 10° to about 80° to a normal to the surface of said laminate and wherein said laminate comprises a paper web.

3. The method of claim 2 wherein said radiation is directed onto the paper web of said laminate and said diffusely reflected intensity value is measured at about the reflectance angle at which the diffusely reflected and scattered radiation reaches its maximum value and at a reflectance angle of about 0° to normal.

4. The method of claim 3 wherein said collimated beam of radiation is modulated by a modulator before being directed onto the paper web of said laminate and the reflected intensity of radiation is measured by a single reflected intensity detector and wherein said laminate comprises a plastic film and said paper web.

5. The method of claim 4 wherein the output signal of said reflected intensity detector is amplified by an amplifier tuned to the frequency of said modulator and said laminate consists of a plastic film and a paper web laminated to each surface of said film.

6. A method for the on-line determination of the bonding strength of a plural layer laminate having at least one outer layer transparent to electromagnetic radiation in the visible, near infrared, or near ultraviolet light portion of the spectrum, said method comprising:
   (a) directing a collimated beam of said electromagnetic radiation through a first polarizer onto the substantially flat surface of said laminate at an incident angle greater than a normal to the surface of said laminate;
   (b) measuring a first diffusely reflected intensity value of said radiation passed through a second polarizer oriented parallel to said first polarizer at about the reflectance angle at which the diffusely reflected and scattered radiation reaches its maximum value;
   (c) measuring a second diffusely reflected intensity value of said radiation at said reflectance angle passed through a third polarizer oriented perpendicular to said first polarizer;

(d) converting the diffusely reflected intensity values to a diffuse intensity ratio derived value which is proportional to the bonding strength of said laminate based on a predetermined relationship of the bonding strength of said laminate to said diffuse intensity ratio derived value.

7. The method of claim 6 wherein said radiation is directed onto said laminate at an incident angle of about 10° to about 80° to normal and said laminate comprises a paper web.

8. The method of claim 7 wherein said diffusely reflected intensity value is measured at about the reflectance angle at which the diffusely reflected and scattered radiation reaches its maximum value for said laminate.

9. The method of claim 8 wherein said radiation is directed onto the paper web surface of said laminate.

10. The method of claim 9 wherein said laminate comprises a plastic film and said paper web, said collimated light is passed through a modulator prior to polarization of said collimated light, and the diffusely reflected intensity value of said light is measured at about the reflectance angle at which the diffusely reflected and scattered radiation reaches its maximum value utilizing a single reflected intensity detector the output signal of which is amplified by an amplifier tuned to the frequency of said modulator.

11. Apparatus for determining the bond strength of a laminate having at least one inner layer and one outer layer, said outer layer being transparent to electromagnetic radiation, comprising:

(a) Means for directing a beam of collimated electromagnetic radiation transmitted onto a surface of said inner layer through said transparent outer layer at an incident angle greater than normal to the surface;

(b) Means for measuring the intensity of said beam of electromagnetic radiation reflected from said laminate at two substantially different diffuse reflectance angles to obtain a derived value which is proportional to said bond strength.

12. The apparatus of claim 11 wherein said electromagnetic radiation has a wave length in the visible, near ultraviolet, or near infrared portion of the spectrum and said means for directing collimated electromagnetic radiation includes a converging lens and a radiation source located at the focal point of said lens.

13. The apparatus of claim 12 wherein said apparatus further comprises:

a modulator for modulating said collimated radiation prior to directing said radiation onto said surface of said laminate.

14. The apparatus of claim 13 wherein the radiation reflected at said two reflection angles is measured by a single detector and a detector output signal is amplified by an amplifier tuned to the frequency of said modulator.

15. The apparatus of claim 14 further comprising: a first polarizer for polarizing said beam of collimated radiation and a second polarizer for polarizing said radiation reflected at said two substantially different diffuse reflectance angles, said second polarizer being capable of (A) polarizing said radiation in a direction parallel to the polarization direction of said beam of collimated radiation or (B) polarizing said radiation in a direction perpendicular to the polarization direction of said beam of collimated radiation.

* * * * *